United States Patent
Manbrini

(10) Patent No.: US 8,376,729 B2
(45) Date of Patent: Feb. 19, 2013

(54) ROLLER COMPACTOR INTEGRATED TO A WHEEL TRACK MACHINE FOR LABORATORY TESTS ON BITUMINOUS MIXES

(75) Inventor: Mario Manbrini, Modena (IT)

(73) Assignee: Mecpart S.p.A., Castelfranco Emilia (MO) (IT)

(*) Notice: Subject to any disclaimer, the term of this patent is extended or adjusted under 35 U.S.C. 154(b) by 0 days.

(21) Appl. No.: 13/018,569

(22) Filed: Feb. 1, 2011

(65) Prior Publication Data
US 2011/0200699 A1 Aug. 18, 2011

(30) Foreign Application Priority Data
Feb. 1, 2010 (IT) .............................. PR2010A0008

(51) Int. Cl.
*B28B 3/12* (2006.01)
(52) U.S. Cl. .......... 425/374; 425/412; 425/425; 73/823; 73/824; 73/856
(58) Field of Classification Search .................. 425/412, 425/317, 374, 425, 432; 73/146, 822, 823, 73/824, 856, 862.55
See application file for complete search history.

(56) References Cited

U.S. PATENT DOCUMENTS

| 3,318,156 | A | * | 5/1967 | Dietert ............................ 73/866 |
| 4,938,055 | A | | 7/1990 | Tsuda |
| 5,036,709 | A | | 8/1991 | McRae |
| 5,366,367 | A | * | 11/1994 | Dekker et al. ................ 425/194 |
| 5,641,901 | A | | 6/1997 | Powell |
| 5,659,140 | A | * | 8/1997 | Jakob et al. .................... 73/788 |
| 5,987,961 | A | | 11/1999 | Harris et al. |
| 6,125,685 | A | | 10/2000 | Collier et al. |

FOREIGN PATENT DOCUMENTS

| CN | 1789961 A | 6/2006 |
| DE | 9303157 U1 | 4/1993 |
| DE | 29610661U1 U1 | 10/1996 |
| JP | 2001059805 A | * 3/2001 |
| JP | 2006170680 A | * 6/2006 |
| WO | 20041034064 A1 | 4/2004 |

OTHER PUBLICATIONS

Timothy W. Voller, Douglas I. Hanson; Development of Labatory Procedure for Mesurement Friction of HMA Mixtures-Phase I; Dec. 2006; NCAY Auburn University; NCAT Report 06-06, pp. 10-19; http://www.eng.auburn.edu/files/centers/ncat/reports/2006/rep06-06.pdf.*
Pierpaolo Viola; Applications of Reclaimed Asphalt Pavement; Sep. 2010; pp. 21-27; http://bll- gdynia.pl/referaty/TECNOTEST.pdf.*
Tecnotest; Roller Compaction and Wheel-Tracking Apparatus; Jun. 2010; Youtube Video:http://www.youtube.com/watch?v=YCTe8rAL8Dw.*
Italian Search Report, dated Sep. 20, 2010, from corresponding Italian application.

* cited by examiner

*Primary Examiner* — Yogendra Gupta
*Assistant Examiner* — Ninh Le
(74) *Attorney, Agent, or Firm* — Young & Thompson

(57) ABSTRACT

An integrated machine for making, in laboratory, slabs made of a controlled-compaction bituminous mix in a mold and for making wheel tracking tests on the same, the compaction is performed by two idle disks which slide and press the side extensions of an array of vertical plates overlapping the mix, the wheel tracking test is performed by a wheel located between the disks; after having removed the array of plates, the wheel can be presented to the mix, since the disks are located at a distance greater than the mold width.

9 Claims, 2 Drawing Sheets

ROLLER COMPACTOR INTEGRATED TO A WHEEL TRACK MACHINE FOR LABORATORY TESTS ON BITUMINOUS MIXES

FIELD OF THE INVENTION

The present invention refers to the experimental field of the bituminous mixes for road paving, and, more specifically, to the machines adapted to the laboratory manufacturing of controlled compaction slabs for executing on them wheel tracking tests or to be cut in elements adapted to advanced tests.

The viscoelastic and thermoplastic behaviour of the bituminous mixes exposes the outer layers of the road flexible paving to the risk of being permanently deformed (wheel trackings) due to the action of the heavy transport in the areas which are more subjected to the tyres rolling, this effect is augmented by an environment temperature rise.

Such deformations impair the smoothness of a road, and therefore the safety of the vehicles running on it.

For characterising the deterioration, the phenomenon of the permanent deformations is studied by road simulators or wheel track machines, capable of reproducing on a reduced scale and under predetermined test conditions, the action of the vehicle load (rolling wheel).

The specimen under test can be directly taken from the road or can be manufactured, in a laboratory, with a slab shape.

For obtaining this slab with the same mechanical characteristics of the paving to be designed, it is necessary another machine, known as "roller compactor", simulating the rolling made in a construction site on the spreaded bituminous mix.

The manufactured slab is also used for other objects: by suitably trimming it, it is possible to obtain specimens adapted to dynamic tests for determining the constitution properties of the material and its fatigue resistance.

The experimental laboratory dedicated to the study of road pavings requires two separate machines: one dedicated to the manufacture of the mix slab for the different tests, the other dedicated to the wheel tracking test on the slab itself.

DISCLOSURE AND ADVANTAGES OF THE INVENTION

The object of the present invention consists of unifying the above mentioned machines.

In brief, the invention consists of an architecture adapted to obtain a single machine having two operations.

The invention refers to a way for integrating two separate machines used in an experimental laboratory which studies bituminous mixes for road paving. Such machines are known respectively as "roller compactor" and "wheel track machine"; the first is for manufacturing controlled-compaction mix slabs, the second for simulating, on a reduced scale, the deforming effect generated by tyres rolling on a road. The reference regulations are EN 12697-33 and EN 12697-22 respectively.

A regulated variant of the roller compactor provides a suitably loaded idle metal cylinder alternatively sliding on a row of slabs freely reciprocally translating in a vertical direction, guided by a container containing the mix. These slabs form a flexible interface adapted to transmit shearing stresses to the mixture contained in the mould.

A regulated variant of the wheel track machine comprises a suitably loaded idle wheel horizontally reciprocally sliding on the mix surface for forming a tracking on it, whose depth is the measure to be studied.

The invention comprises the substitution of the conventional cylinder of the compactor with two facing disks located at a distance greater than the size of the mould and the application of two side projecting extensions to the slabs, in order to form sliding tracks of said disks. This arrangement consists of housing between the two disks the wheel dedicated to the wheel tracking. This wheel can be driven to the mix surface once the slabs have been removed, since the distance between the disks is greater than the mould width.

In this way, all the handling, loading, control, and measuring devices are available both for the compaction and the wheel tracking.

The advantage brings about a substantial cost reduction for a laboratory. The measuring and control devices necessary for the wheel tracking operation are also available for the roller compactor, which can also be controlled for performing specific experimental procedures which are not expressively anticipated in the reference regulation.

Said object and advantages are all met by the machine object of the present invention, which is characterized for what it is claims in the attached claims.

BRIEF DESCRIPTION OF THE DRAWINGS

The attached drawings, as an exemplifying non limiting example, are the reference for the following description; in particular.

PRIOR ART

Figure 1:
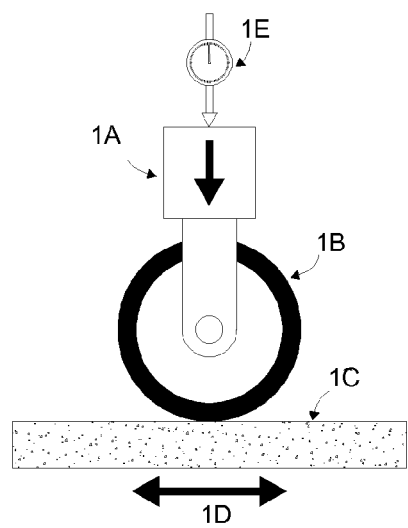
FIGS. 1, 2 and 3 show examples of the prior art.

Referring to the wheel track machine, the EN 12697-22 regulation describes the different possible arrangements and the associated test modes. The more common arrangement, as shown in FIG. 1, provides a test room at a controlled temperature, receiving a device (1A) generating a constant load on a freely rotating tired wheel (1B) around its horizontal axis. Said wheel abuts on the sample (1C) which in turn is subjected to cyclical movements along a rectilinear and horizontal path (1D). The depth of the tracking formed by the specimen surface after a predetermined number of passes provides the expected measurement (1E).

Figure 2:
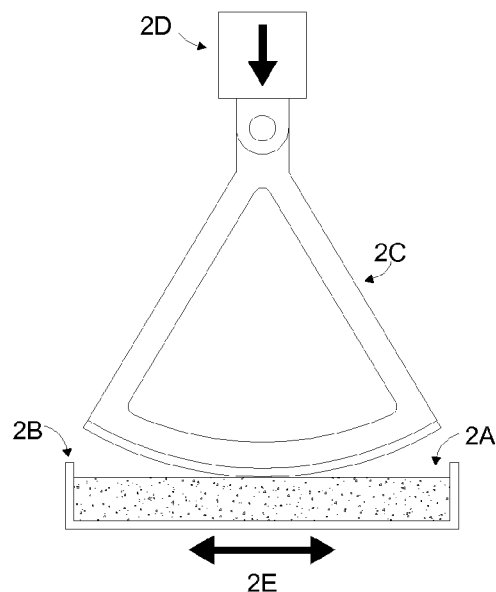

Regarding the roller compactor, the reference regulation EN 12697-33 lists different approaches; the more simple approach, FIG. 2, provides the mix (2A) inside a mould (2B) upwardly closed by a sector of a cylinder (2C), on the cylinder rotation axis acts the load device (2D). The sector is moved with a pendular motion dragged by the alternative rectilinear motion (2E) received by the mould.

The compacting action on the mix is the same as the one performed by a road roller moving backwards and forwards on the spreaded bituminous mix.

The problems of this arrangement are different.

First of all, the cylinder sector does not need to move along the whole mouth of the mould, so it leaves at the ends of the travel a space sufficient for the grains possibly ejected by the mixture; the result is a slab having two edges which are not suitably compacted.

Secondly, the cold surface of the cylinder sector lowers the mix temperature and, consequently, lowers the mobility of the binder inside the contact layer, in this way it increases the non homogeneity in the product.

Figure 3:
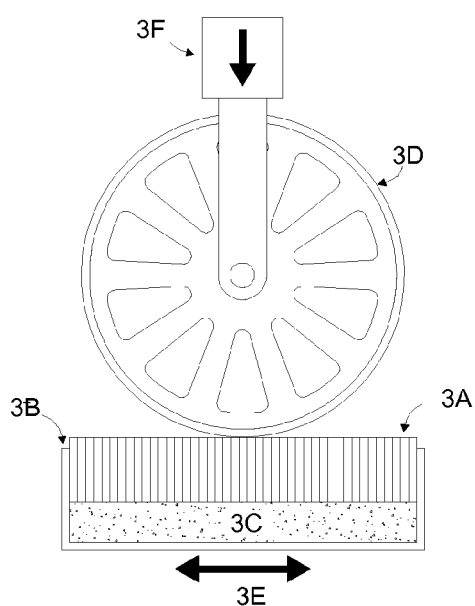

The regulation itself offers a valid alternative for avoiding said disadvantages, by outlining a flexible interface between the roller and the mix (as shown in FIG. 3).

There is a pack of metal slabs (3A) vertically arranged to close the mould (3B) and which can freely reciprocally translate guided by the walls of the latter.

Such system avoids the ejection of the mix grains (3C), by allowing the roller (3D) to follow the whole path on the slab series when it is performed the movement (3E) and, therefore, to subject the whole sample to the effect of the load produced by a jack (3F).

The slabs pack can then be pre-heated with the mould to the temperature of the mix, in order to have a closed container at a high heat inertia for making negligible the cooling of the bitumen during the compaction.

DESCRIPTION OF THE INVENTION

Figure 4:
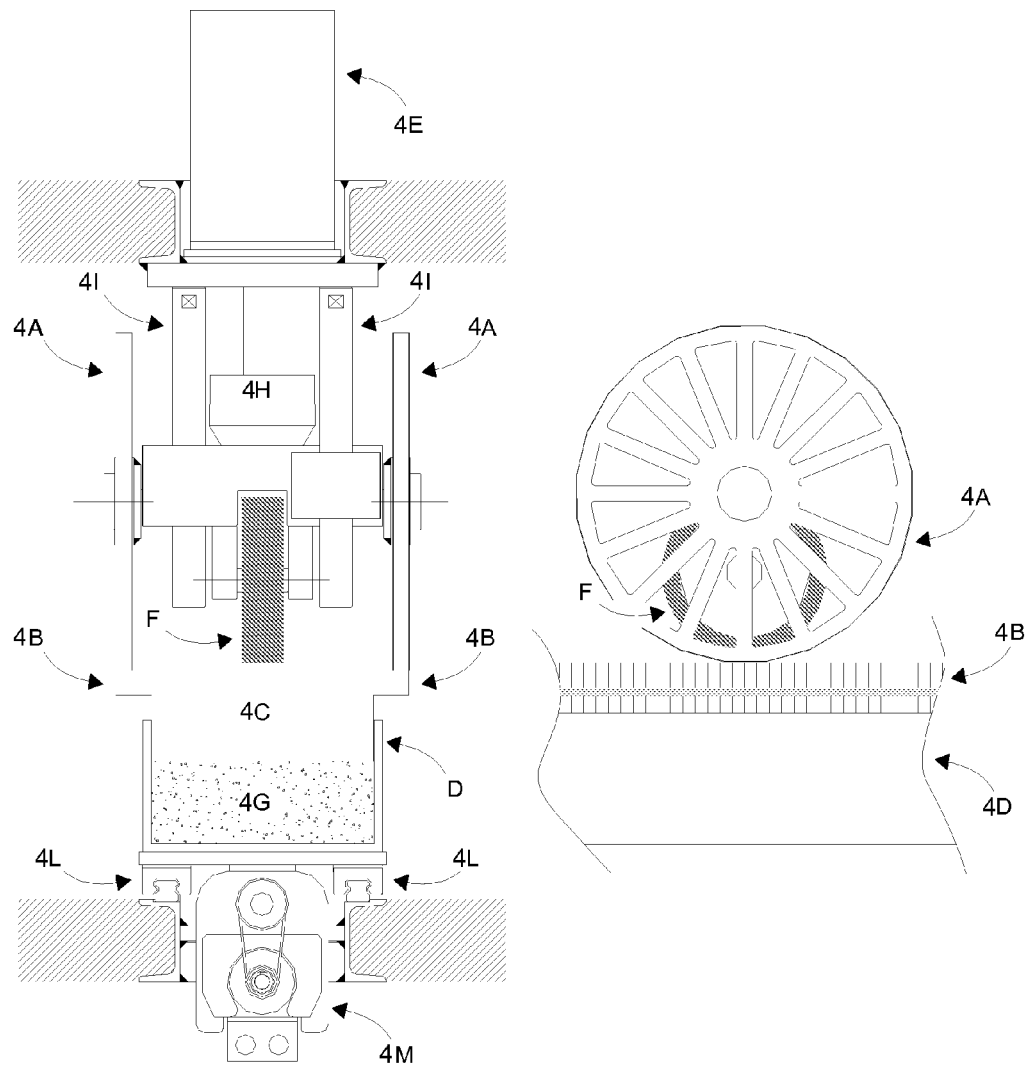
FIG. 4 shows the machine of the invention.

FIG. 4 shows a schematic view of the machine of the invention and substantially illustrates the invention, which consists in an arrangement adapted to obtain a single machine having two operations.

The cylindrical roller characterizing the machines of the prior art is formed by two coaxial facing idle disks 4A; two side projecting extensions 4B are added to the rectangular-shaped slabs equipping said machines for obtaining the 4C shape.

The distance between the disks is such to be greater than the side of the mould 4D, so that, after the removal of the slabs series and after the mix has been taken to the surface in the container, the jack 4E can cause the central wheel 4F to contact the mix surface 4G, while the disks freely lower besides the upper edge of the mould.

The remaining references indicate the dynamometer 4H, the vertically sliding guides 4I, the horizontally sliding guides 4L and the associated motor 4M.

The figure does not comprise the vertical displacement sensor, the power, control and driving devices, the tough frame and the thermostatically-controlled protective covering.

In brief, the slab extensions 4B form the sliding tracks of the disks 4A and therefore enable the use of the cited devices for compacting the mix slab; by removing the slabs 4C, it is possible to obtain the central wheel 4F which, with the loading, control and measuring devices, allows the wheel tracking test.

The invention claimed is:

1. An integrated machine for making, in a laboratory, slabs made of a controlled-compaction bituminous mix, comprising:
   a mould (4D) configured for holding a bituminous mix (4G) with a bituminous mix upper surface, the mould (4D) having an upper edge and side walls, the side walls having facing surfaces separated by a first distance and that define a bituminous mix upper surface width;
   a cylindrical roller formed by
   i) two coaxial facing idle disks (4A), facing surfaces of said two coaxial facing idle disks (4A) being separated by a second distance,
   ii) a removable slab (4C) located below the two coaxial facing idle disks (4A) and above the mould (4D), the slab (4C) comprising two side projecting extensions (4B), the slab having side surfaces extending from a lower surface of the two side projecting extensions (4B) and a lower surface of the slab, the slab having an upper surface width greater than a width of the lower surface width by an amount equal to a width of the two side projecting extensions, the two side projecting extensions (4B) being located in alignment directly below the two coaxial facing idle disks (4A), the lower width of the slab (4C) corresponding to the bituminous mix upper surface width within the mould (4D), and
   iii) a central wheel (4F) located between the two coaxial facing idle disks (4A),
   wherein the second distance separating the facing surfaces of said two coaxial facing idle disks (4A) is greater than the first distance of the mould's facing surfaces; and
   a jack (4E) position to cause the central wheel (4F), with the slab (4C) removed, to contact the bituminous mix upper surface while said two coaxial facing idle disks (4A) freely lower besides the upper edge of the mould outside exterior surfaces.

2. The integrated machine of claim 1, wherein said central wheel (4F) and said two coaxial facing idle disks (4A) are configured for reciprocating translating motion.

3. The integrated machine of claim 1, further comprising:
   a dynamometer (H) and vertically sliding guides (4I) located between the two coaxial facing idle disks (4A); and
   horizontally sliding guides (4L) and an associated motor (4M) located below said mould (4D).

4. The integrated machine of claim 1, wherein the two side projecting extensions (4B) are arranged as sliding tracks of the two coaxial facing idle disks (4A).

5. The integrated machine of claim 1, wherein the central wheel (4F) is configured for a wheel tracking test.

6. An integrated machine for making, in a laboratory, slabs made of a controlled-compaction bituminous mix, comprising:
   a mould (4D) configured for holding a bituminous mix (4G) with a bituminous mix upper surface, the mould (4D) having an upper edge and side walls with exterior surfaces and interior facing surfaces separated by a first distance, the first distance defining a bituminous mix upper surface width;
   a cylindrical roller formed by
   i) two facing coaxial idle disks (4A), facing surfaces of said two coaxial idle disks (4A) being separated by a second distance,
   ii) a removable slab (4C) located below the two coaxial facing idle disks (4A) and above the mould (4D), the slab (4C) comprising two projecting side extensions (4B), the slab having side surfaces extending from a lower surface of the two side side extensions (4B) and a lower surface of the slab, the slab having an upper surface width greater than a width of the lower surface width by an amount equal to a width of the two side extensions, the lower width of the slab (4C) corresponding to the bituminous mix upper surface width within the mould (4D), and
   iii) a central wheel (4F) located between the two coaxial idle disks (4A),
   wherein the central wheel and the two coaxial idle disks are configured to move together in a vertical direction, and
   wherein the second distance separating the facing surfaces of said two coaxial idle disks (4A) is greater than the first distance of the mould's facing surfaces; and
   a jack (4E) position to vertically move the central wheel (4F), with the slab (4C) removed, to contact the bituminous mix upper surface to perform a wheel tracking test and said two coaxial facing idle disks (4A) freely lower besides the upper edge of the mould outside exterior surfaces.

7. The integrated machine of claim 6, wherein
said central wheel (4F) and said two coaxial facing idle disks (4A) are configured for reciprocating translating motion.

8. The integrated machine of claim 7, further comprising:
a dynamometer (H) and vertically sliding guides (4I) located between the two coaxial facing idle disks (4A); and
horizontally sliding guides (4L) and an associated motor (4M) located below said mould (4D).

9. The integrated machine of claim 7, wherein the two side projecting extensions (4B) are arranged as sliding tracks of the two coaxial facing idle disks (4A).

* * * * *